(12) United States Patent
McIntosh et al.

(10) Patent No.: US 6,339,648 B1
(45) Date of Patent: Jan. 15, 2002

(54) IN-EAR SYSTEM

(75) Inventors: Ian McIntosh, Alexandria; Roger Leon George Saulce, Montreal, both of (CA)

(73) Assignee: Sonomax (SFT) INC, Montreal (CA)

(*) Notice: Subject to any disclaimer, the term of this patent is extended or adjusted under 35 U.S.C. 154(b) by 0 days.

(21) Appl. No.: 09/533,258

(22) Filed: Mar. 23, 2000

(30) Foreign Application Priority Data

Mar. 26, 1999 (CA) .............................................. 9907050

(51) Int. Cl.$^7$ .............................................. H04R 25/00
(52) U.S. Cl. ....................... 381/328; 381/380; 381/322; 181/130
(58) Field of Search ................................ 381/312, 322, 381/328, 329, 380, 381, 382, FOR 133, FOR 135; 181/130, 135

(56) References Cited

U.S. PATENT DOCUMENTS

| | | | |
|---|---|---|---|
| 2,535,258 A | 12/1950 | Bland | 181/23 |
| 2,719,523 A | 10/1955 | Von Gierke | 128/152 |
| 2,803,247 A | 8/1957 | Zwiklocki | 128/152 |
| 3,097,059 A | 7/1963 | Hoffman | 18/55.05 |
| 3,344,220 A | 9/1967 | Cook | 264/222 |
| 3,408,461 A * | 10/1968 | Langford | 381/328 |
| 3,440,314 A | 4/1969 | Frisch | 264/222 |
| 3,602,654 A | 8/1971 | Victoreen | 179/182 |
| 3,736,929 A | 6/1973 | Mills | 128/152 |
| 3,782,379 A | 1/1974 | Lampe | 264/222 |
| 3,783,864 A | 1/1974 | Mouer | 128/152 |
| 3,852,540 A * | 12/1974 | Diethelm | 381/328 |
| 3,881,570 A | 5/1975 | Lewis | 181/135 |
| 4,006,796 A | 2/1977 | Coehorst | 181/130 |
| 4,051,330 A | 9/1977 | Cole | 179/107 |
| 4,060,080 A | 11/1977 | Akiyama | 128/152 |
| 4,133,984 A | 1/1979 | Akiyama | 179/107 |
| 4,353,364 A | 10/1982 | Woods | 128/152 |
| 4,375,016 A | 2/1983 | Harada | 179/182 |
| 4,459,247 A | 7/1984 | Rothemund | 264/22 |
| 4,540,063 A | 9/1985 | Ochi et al. | 181/135 |
| 4,607,720 A | 8/1986 | Hardt | 181/135 |
| 4,712,245 A | 12/1987 | Lyregaard | 381/68.6 |
| 4,716,985 A | 1/1988 | Haertl | 181/130 |
| 4,800,636 A | 1/1989 | Topholm | 29/169.5 |
| 4,807,612 A | 2/1989 | Carlson | 128/868 |
| 4,811,402 A | 3/1989 | Ward | 381/68.6 |
| 4,834,211 A | 5/1989 | Bibby et al. | 181/135 |
| 4,860,362 A * | 8/1989 | Tweedle | 381/328 |
| 4,870,688 A | 9/1989 | Voroba et al. | 381/60 |
| 4,880,076 A | 11/1989 | Ahlberg et al. | 181/130 |
| 4,901,353 A | 2/1990 | Widin | 381/68 |
| 4,937,876 A | 6/1990 | Biŝrmans | 381/68.6 |
| 4,962,537 A * | 10/1990 | Basel et al. | 381/328 |
| 4,975,967 A | 12/1990 | Rasmussen | 381/187 |
| 5,002,151 A | 3/1991 | Oliveira et al. | 181/130 |
| 5,006,055 A | 4/1991 | Lebisch et al. | 425/2 |
| 5,008,058 A | 4/1991 | Hanneberger et al. | 264/134 |

(List continued on next page.)

FOREIGN PATENT DOCUMENTS

| | | | |
|---|---|---|---|
| JP | 61-238198 | 7/1986 | H04R/25/02 |
| WO | WO99/31934 | 6/1999 | H04R/25/00 |
| WO | WO99/31935 | 6/1999 | H04R/25/00 |

OTHER PUBLICATIONS

E–A–R Classic, 1994.
Aearo E–A–E, 1997.

*Primary Examiner*—Curtis Kuntz
*Assistant Examiner*—Suhan Ni

(57) ABSTRACT

The device comprises a core, surrounded by a thin sheath so as to form a chamber that can be inflated. Inflation is done while the device is inside the ear, using an inflation tool. The tool injects a solid-setting fluid into the chamber. After curing, the tool is detached, leaving a finished in-ear unit, upon which no further manufacturing processing is required.

11 Claims, 6 Drawing Sheets

U.S. PATENT DOCUMENTS

| | | | |
|---|---|---|---|
| 5,044,373 A | 9/1991 | Northeved et al. ............ 28/746 |
| 5,045,266 A | 9/1991 | Moro et al. .................. 264/222 |
| 5,068,902 A | 11/1991 | Ward ......................... 381/68.6 |
| 5,131,411 A | 7/1992 | Casali et al. ................... 12/864 |
| 5,185,802 A | 2/1993 | Stanton ..................... 381/68.6 |
| 5,201,007 A | 4/1993 | Ward et al. ................. 381/68.6 |
| 5,259,032 A | 11/1993 | Perkins ........................ 381/68 |
| 5,321,757 A | 6/1994 | Woodfill, Jr. ................. 381/68 |
| 5,333,692 A | 8/1994 | Casali et al. ................ 128/864 |
| 5,357,576 A * | 10/1994 | Arndt ........................ 381/328 |
| 5,440,082 A | 8/1995 | Claes ......................... 181/135 |
| 5,455,994 A | 10/1995 | Termeer et al. ............ 29/169.5 |
| 5,483,027 A | 1/1996 | Krause ....................... 181/135 |
| 5,645,074 A | 7/1997 | Shennib et al. ............. 128/746 |
| 5,659,156 A | 8/1997 | Mauney et al. ............. 181/130 |
| 5,718,244 A | 2/1998 | Thornton .................... 128/864 |
| 5,804,109 A | 9/1998 | Perkins ...................... 264/40.1 |
| 6,022,311 A | 2/2000 | Juneau et al. ................. 600/25 |
| 6,094,494 A * | 7/2000 | Haroldson .................. 381/328 |

* cited by examiner

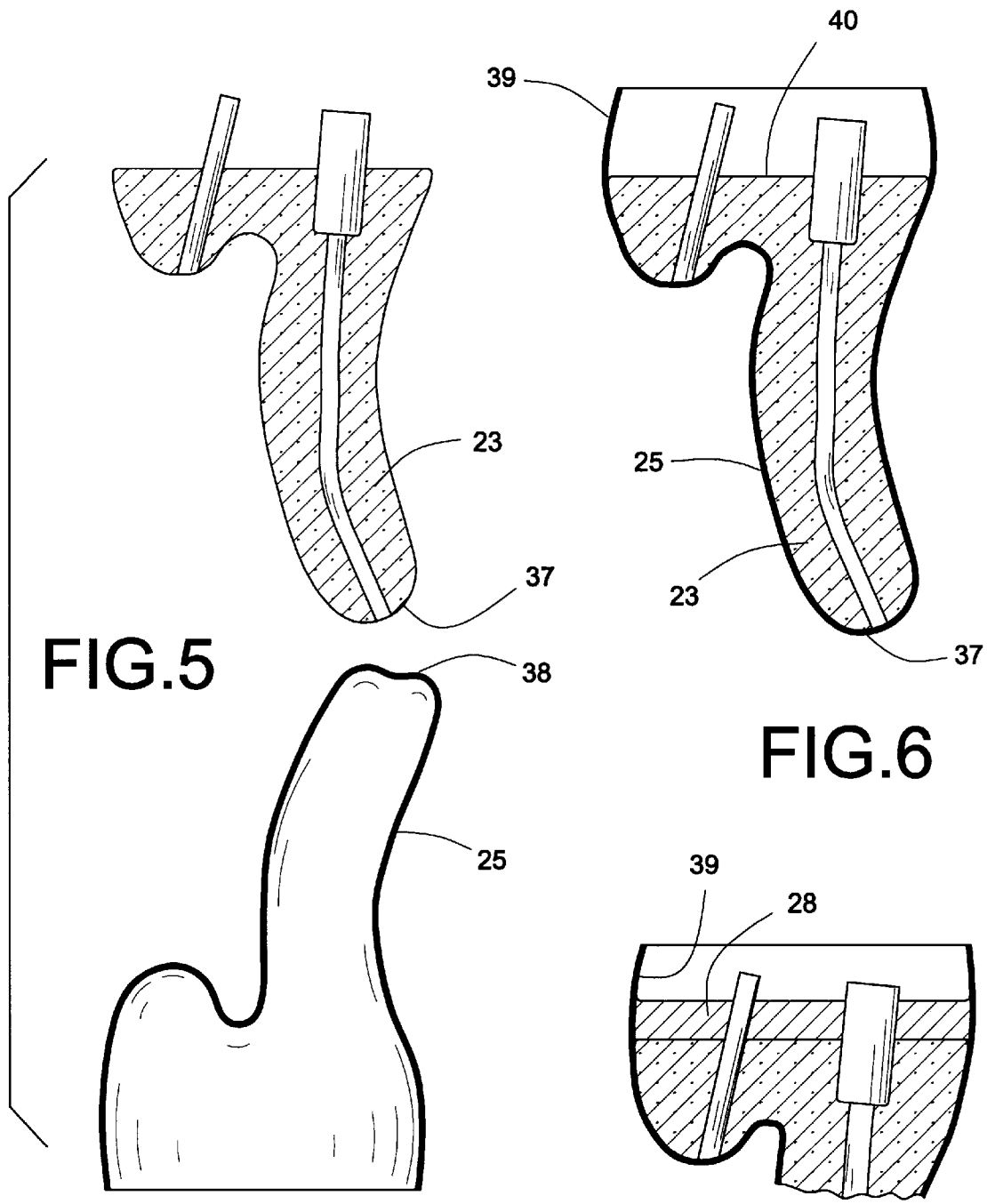

IN-EAR SYSTEM

This invention relates to in-ear hearing devices, and relates to the fitment, in the ear, of such devices. In this context, the term hearing device includes hearing protection devices, for preventing loud noises from damaging a person's hearing, particular in the work-place; and includes hearing aids.

Hearing protection devices are often passive (i.e not powered) and some may simply amount to a plug in the ear; while more sophisticated (but still passive) HPDs may include acoustic chambers and filters, for passing or attenuating selected frequencies.

The term hearing device includes active devices—either of a hearing protection nature, or of a hearing aid nature—in which the some or all of the batteries and other components are mounted behind the ear, or remotely, in a box, which communicates with the in-ear unit by means of a sound-tube, or by wires; and includes active devices in which a microphone, speaker, and all the associated sound-processing circuitry and components, including a battery, are contained within the in-ear unit.

BACKGROUND TO THE INVENTION

It is recognised that the performance of all in-ear hearing devices, both noise-protectors and hearing-aids, is highly dependent upon the fit of the device in the ear. Conventionally, it has generally been the case that an in-ear hearing-aid is custom-fitted to the individual patient or client. However, custom-fitting is an expensive and time-consuming process. The custom-fitting process is so cumbersome that accepting a poor fit often seems a better alternative than going through the fitting process again.

Using the conventional custom-fitment system, a well-fitting hearing-aid can provide excellent performance; however, the problem is that many hearing-aids do not fit properly. Thus the traditional problem has been in a lack of consistency as to the quality of the physical fit. Recent trends in digital hearing devices seek to overcome the traditional inconsistency-of-fit problem by providing multi-channel sound transmission, one of the channels being used to prevent feed-back. The invention seeks to overcome the traditional inconsistency-of-fit problem by making it possible for the fit to be consistently good.

Conventional custom-fitment, as a process, is somewhat unpleasant, requiring that wet silicone be injected into the ear. The silicone impression of the ear-canal is then sent away to a manufacturing facility, and it can take several weeks, after the fitting appointment, to produce the in-ear device. Also, the custom-fitment aspect of the consultation often takes an inordinate part of the hearing-health-practitioner's (not to mention the client's) time, which might perhaps be better spent on evaluation and refinement.

Millions of workers in industry are exposed to noise levels that can damage their hearing. Of course, hearing protection devices are available. However, individual or custom-fitment of conventional HPDs has been problematic and expensive. Conventionally, HPDs have therefore had to be provided on a one-size-fits-all basis, or at least on the basis of a few sizes fit all. If an individual person happened not to fit the range of standard shapes and sizes available, his hearing was not as well protected.

Another problem with conventional HPDs is that it is difficult to tell just what is the performance of the device. The HPD might be very good, theoretically, at preventing sound at one end of the HPD from reaching the other end of the HPD, but if the HPD is a poor fit, sound simply by-passes around the HPD. The tendency therefore is for the HPD to be too tight, which leads to poor wearer-comfort, whereby the wearer tends not to keep the HPD in for long periods.

Whereas a conventional custom-fitted in-the-ear hearing-aid is of hard rigid moulded plastic, conventional HPDs generally have been of flexible construction, being resiliently compressible. The compressible HPD is squeezed into the ear-canal, where it expands, and fills the canal. However, during use, the constant pressure outwards, against the ear-canal, is uncomfortable, and again the wearer tends not to want to keep the HPD in for long periods.

From a factory-safety standpoint, verification of proper initial fitment, and of proper day-to-day wear fitment, is very difficult with the conventional HPDs. Inspections by safety officers are subjective, and are of little use as evidence of proper fitment and use, and still less of effectiveness. An improper fit results in poor protection, as well as discomfort for the user, which in turn encourages non-compliance with hearing protection programs.

From the performance standpoint, HPDs, like hearing-aids, really have to be custom-fitted. This is generally acknowledged as a fact. But, conventionally, custom-fitting of HPDs could hardly be justified on economic grounds.

The invention is aimed at providing a system for fitting devices into the ear, in which the performance of the device is maximised, insofar as the performance is affected by the good fit of the device in the ear-canal, but in which the above mentioned disadvantages as to cost and cumbersomeness of the fitment process are minimised.

As will become clear, the fitment process as described herein is so effective, and yet so inexpensive, and so fast, that the system is economically and practically suitable for the custom-fitment of HPDs having excellent performance to the whole work force personnel of a factory.

When the invention is applied in the field of hearing-aids, because the fitment process is so rapid, and so easy, the practitioner can try the client out with several types and configurations of hearing-aid, each of which can, if so desired, be evaluated by the practitioner, and by the client, there and then, all in a single consultation session. As a result, it can be expected that the percentage of clients who receive close to the maximum possible hearing benefit that can be obtained, given the current state of hearing-aid technology, will be much higher than hitherto.

As mentioned, recent developments in digital hearing aids are aimed at by-passing the need for a good fit, by eliminating feedback. However, the likelihood of consistently good fits, which is an aim of the invention, opens up other avenues of development. In fact, it has been suggested that the audio side of hearing-aid technology, especially for the mass market, has become stalled, in the sense that there is little point in developing components of greater performance, because the devices often fit so poorly in the ear that enhanced performance could hardly be utilised. The expectation that a good fit can be achieved quickly, every time, gives a new incentive to the development of the audio side of hearing-aid (and hearing-protection) technology.

DETAILED DESCRIPTION OF PREFERRED EMBODIMENTS

By way of further explanation of the invention, exemplary embodiments of the invention will now be described with reference to the accompanying drawings, in which:

FIG. 5 is a diagram illustrating the assembly of the skin of FIG. 4 over the core-form of FIG. 3.

FIG. 6 is a section showing the sub-assembly of the skin over the core-form.

FIG. 7 is a section showing the addition of an end-plug to the sub-assembly of FIG. 6.

Figure 1:
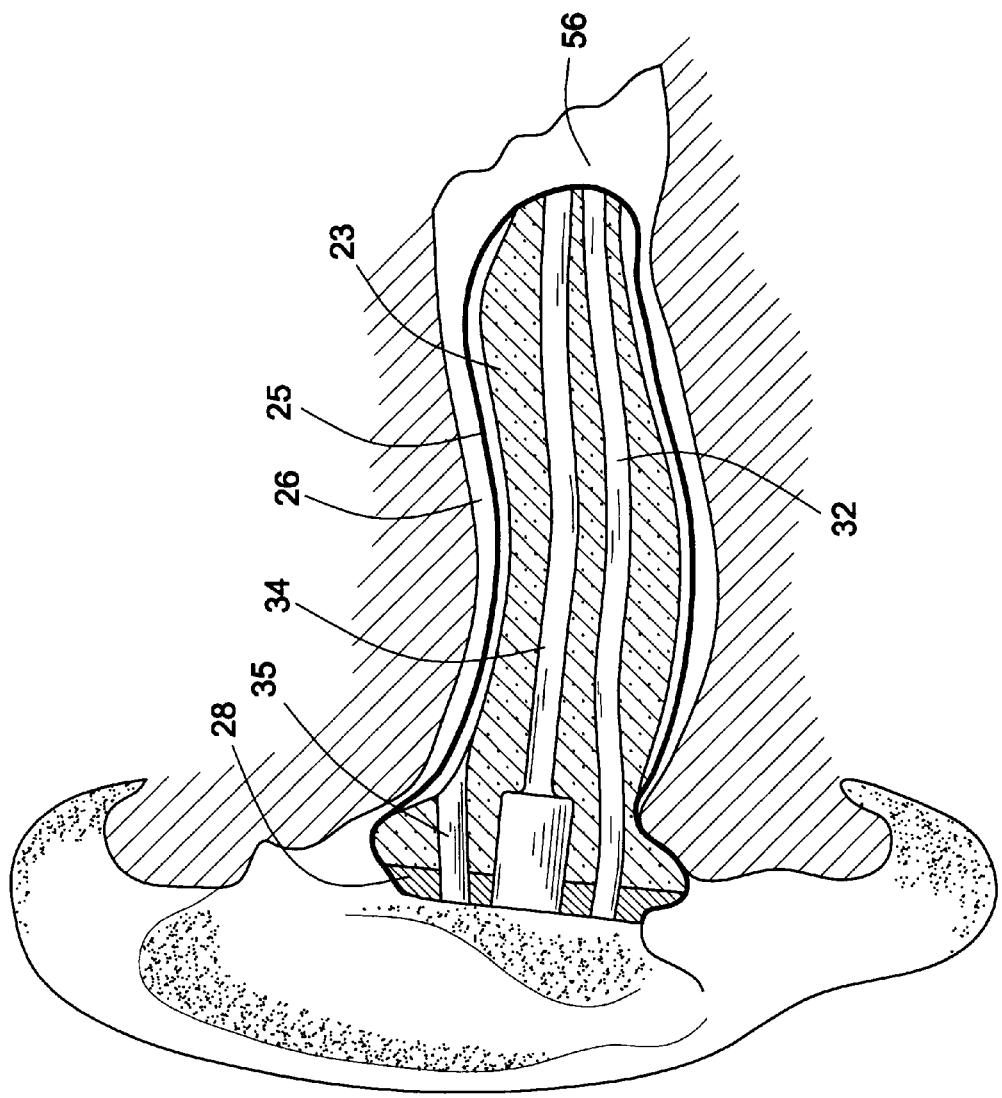
FIG. 1 is a cross-section of an in-ear hearing device that embodies the invention, shown at a preliminary stage of fitment into the ear.

The apparatus shown in the accompanying drawings and described below are examples which embody the invention. It should be noted that the scope of the invention is defined by the accompanying claims, and not necessarily by specific features of exemplary embodiments.

The hearing device 20 shown in the drawings has the following components: a core-form 23; various tubes that are disposed within the core-form; a skin or sleeve or sheath 25; an enclosed and sealed cavity 26 in the annular space between the core-form 23 and the sheath 25; a port that communicates with the cavity 26 for receiving an inflation-fluid into the cavity; and an end-plug 28.

Figure 2:
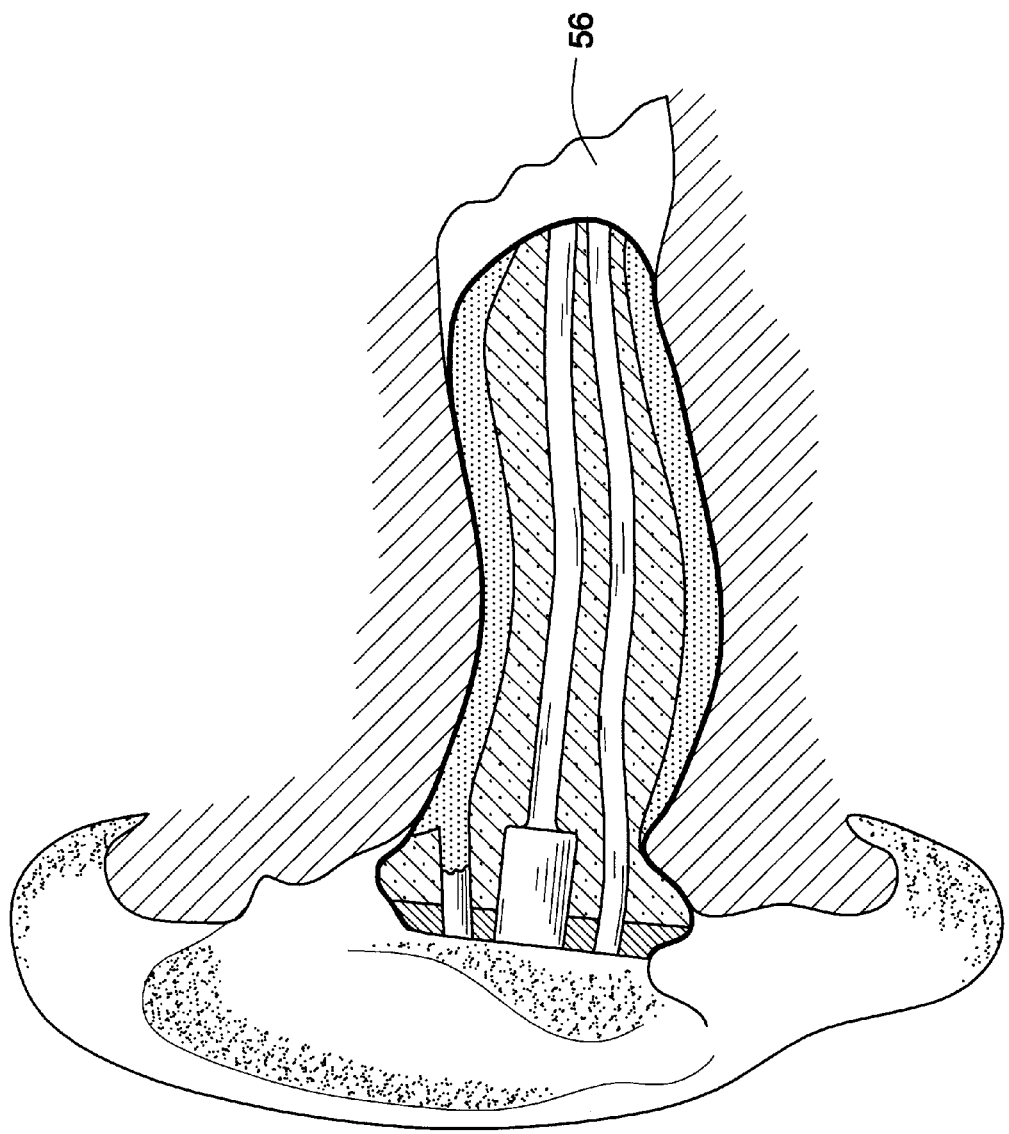
FIG. 2 is the same view as FIG. 1, but shows the device at a later stage of fitment.
Figure 4:
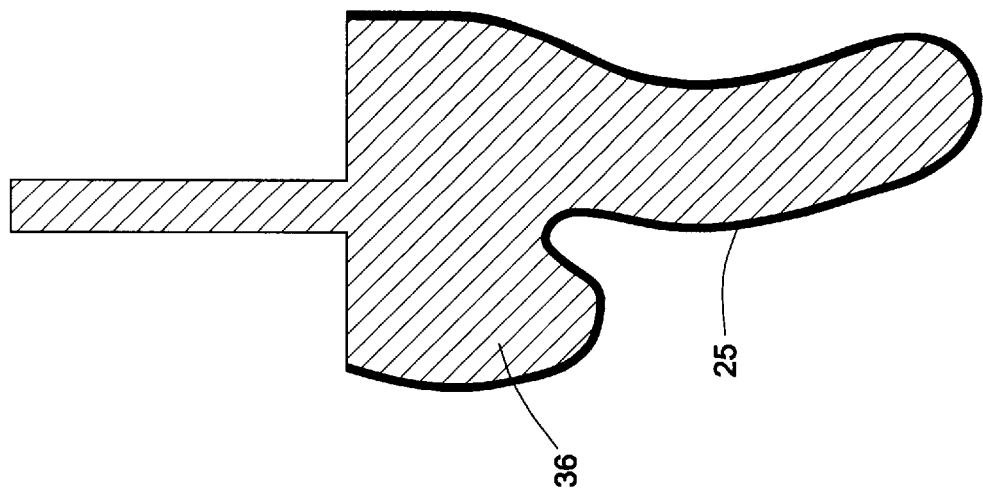
FIG. 4 is a cross-section of a mould, in which is formed a skin or sheath of the hearing device of FIG. 1.

FIG. 1 shows the hearing device 20 after insertion into the ear, but with the cavity 26 empty. FIG. 2 shows the device after the sheath has been inflated by injecting inflation-fluid into the cavity 26. The inflation-fluid is solidifiable or settable, and sets within a few minutes of injection.

Figure 3:
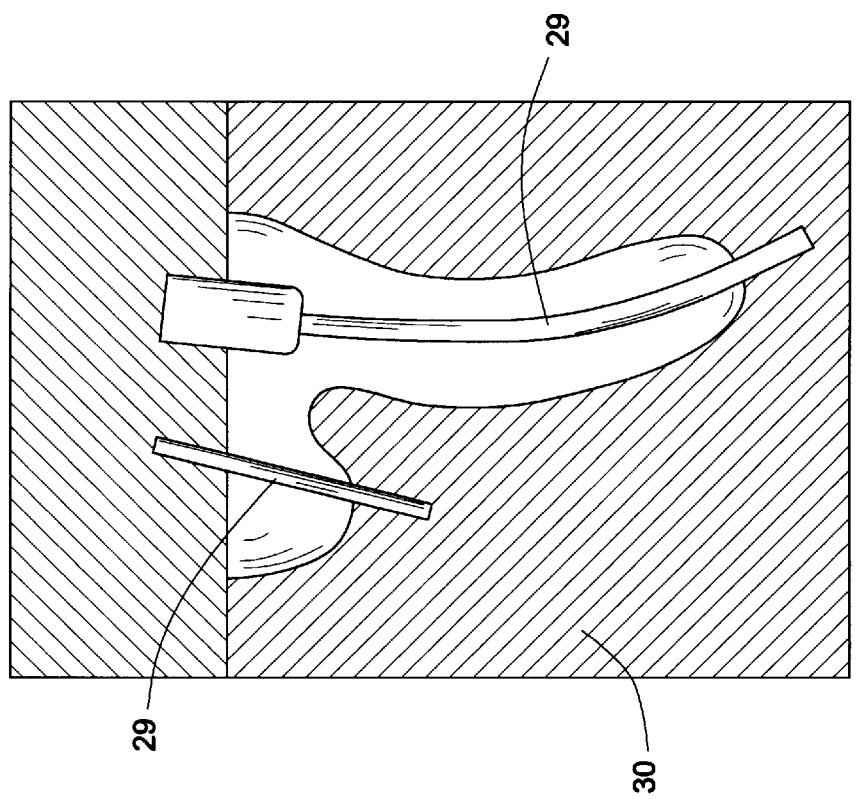
FIG. 3 is a cross-section of a mould, in which is formed a core-form of the hearing device of FIG. 1.

As shown in FIG. 3, the core-form 23 is manufactured by being injection-moulded from polyurethane foam. Cores 29 are included in the mould 30. The cores 29 are later removed, and plastic tubes are inserted into the holes left thereby. The tubes are for communicating the different zones of the core-form 23, and include an access-tube 32, an acoustic-tube 34, and an inflation-tube 35.

Alternatively, the tubes themselves can be inserted into the mould 30, and the core-form is injection-moulded directly around the tubes.

The finished moulded core-form 23 should have the characteristic of being quite soft. That is to say, when the core-form is held between finger and thumb, the core-form can be collapsed by hand pressure. The material should be resilient, so that the core-form immediately regains its moulded shape upon being released. The material preferably is moulded as a soft, resilient, sponge-like, closed-cell foam.

The sheath 25 is manufactured in a water-based polyurethane, by dip-moulding. The male mould 36 around which the sheath is to be formed is dipped first into an appropriate release agent, and then into the liquid plastic from which the sheath is to be formed; after a few moments, the mould is withdrawn, and the still-liquid plastic forms a skin, which quickly solidifies. After curing, the skin is peeled off, i.e unrolled from, the mould. Of course, skilled care and attention is required to ensure the required quality of the moulded sheaths; however, the sheaths are manufactured in a similar manner to that of the conventional thin plastic gloves that are in everyday use by medical professionals.

Water-based polyurethane is non-toxic, and has been used in countless prolonged-contact-with-skin applications.

FIG. 5 shows the sheath 25 being assembled over the core-form 23. The sheath 25 is inside-out in FIG. 5. The bottom end of the tube 34 has been trimmed flush with the material of the core-form 23, and a little adhesive-sealant 37 is smeared over the bottom end of the core-form, over the area surrounding the end of the tube 34.

The inside-out sheath is applied to the core-form, so that the area 38 of the sheath sticks to the adhesive. Then, the rest of the sheath is progressively turned right-side-out, over the core-form, until it en-shrouds the core-form. FIG. 6 shows this condition.

It will be noted that the sheath 25 has a long skirt 39, which protrudes beyond the end-face 40 of the core-form. The end-plug 28 (FIG. 7) is formed by pouring a quantity of (self-levelling) liquid epoxy onto the end-face 40, and leaving it to set.

After curing, the end plug 28 sets hard and solid, and is firmly adhered to the end-face 40 of the core-form 23 and to the skirt 39 of the sheath 25 (FIG. 7).

To ensure a robust securement of the skirt to the end-plug, the edges of the end-face 40 were left slightly rounded; also the liquid plastic from which the end plug solidified had a natural meniscus; whereby the adherence-length over which the end-plug sticks to the skirt, is longer than the nominal thickness of the end-plug.

The skirt 39 and protruding tubes are trimmed and smoothed, bearing in mind that the end-plug 28 will usually be visible when the finished hearing device is inserted in the ear.

As to dimensions, the designer should specify that the material of the sheath has a thickness in the range of about 0.1 mm to 0.15 mm, in a typical case. The end-plug will have a thickness, typically, of about 1.5 mm to 2 mm.

As mentioned, at the points where the tubes emerge from the hearing device, the sheath should be sealed; the inflation-fluid is to be injected into the cavity 26 between the core-form and the sheath, and so the cavity must be sealed against leakage.

Figures 8, 9:
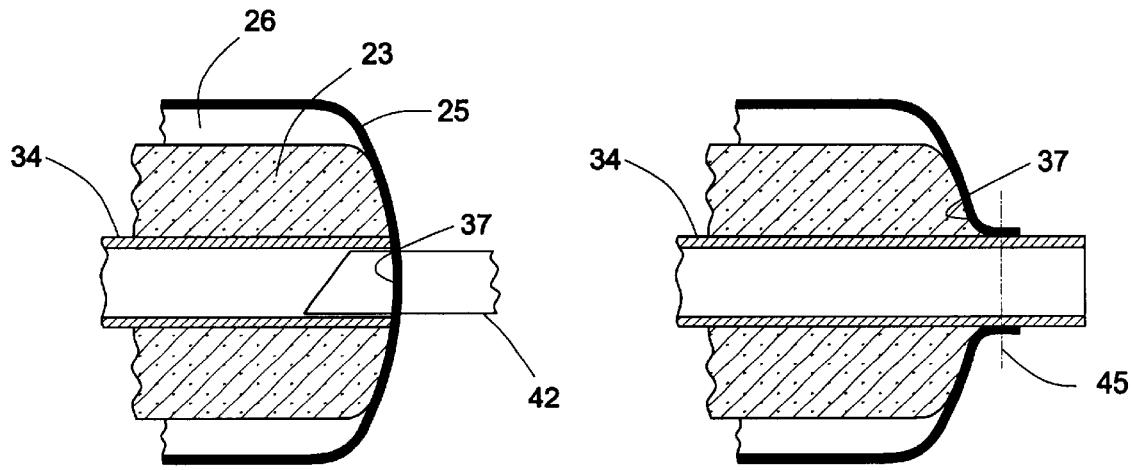
FIG. 8 is a section that shows a manner of securing and sealing a tube into a hearing device that embodies the invention.
FIG. 9 is a section that shows an alternative manner of securing and sealing a tube.

FIG. 8 shows a preferred manner of sealing the acoustic tube 34 to the core-form and to the sheath. As mentioned, the tube 34 is carefully trimmed flush with the end of the core-form, and then adhesive 37 is smeared over the end of the core-form. The material of the sheath 25 sticks to the adhesive 37, over the area of contact as indicated in FIG. 8. After the sheath has been attached, the portion of the sheath material that lies over the end of the tube is pierced by a probe 42, and trimmed to conform to the end of the tube.

In FIG. 9, the end of the tube 34 was left protruding from the end of the core-form 23. Before assembling the sheath to the core-form, a hole is pierced into the area 38 (FIG. 5) of the inside-out sheath, which enables the sheath to be assembled over the end of the core-form in the manner as shown in FIG. 9. Now, the end of the tube and the sheath are cut off together, in the trim-plane 45 as shown. Again, adhesive-sealant is smeared over the end of the core-form, which sticks the sheath to the area of the core-form surrounding the tube.

Either the FIG. 8 or the FIG. 9 system for sealing the tube, sheath, and core-form together are considered easy enough and reliable enough that, upon injection of the inflation-fluid, there is little likelihood that the sheath 25 might separate from the core-form 23. Similarly, there is little likelihood that the sheath might separate from the end-plug 28.

For fitting the device into the ear, first the uninflated device is inserted into the ear-canal. The practitioner examines the client's ear-canal, and selects a core-form of the appropriate size. The practitioner will have stocks of, say, half a dozen different standard sizes of the pre-made core-forms, each with sheath 25, end-plug 28, and tubes attached.

The core-form, with sheath, end-plug, and tubes attached, is inserted into the ear, as shown in FIG. 1. Then, the practitioner injects the inflation-fluid through the inflation-tube 35, and into the cavity 26 between the sheath and the core-form. In FIG. 1 and the other drawings, the sheath is shown clear of, i.e loose on, the core-form, but this is just to illustrate the location of the cavity 26: actually, the sheath is a tight fit on the core-form, to the extent that there is substantially no air between the outside of the core-form 23 and the inside of the sheath 25. Thus, when the sheath is expanded away from the core-form by the injection of the inflation-fluid, there is no air that needs to be vented, and so no provision is required for venting the cavity 26.

The inflation-fluid can be injected by means of a syringe, in the manner that is familiar to practitioners from taking impressions of the ear for conventional custom-moulded hearing aids.

Figure 10:
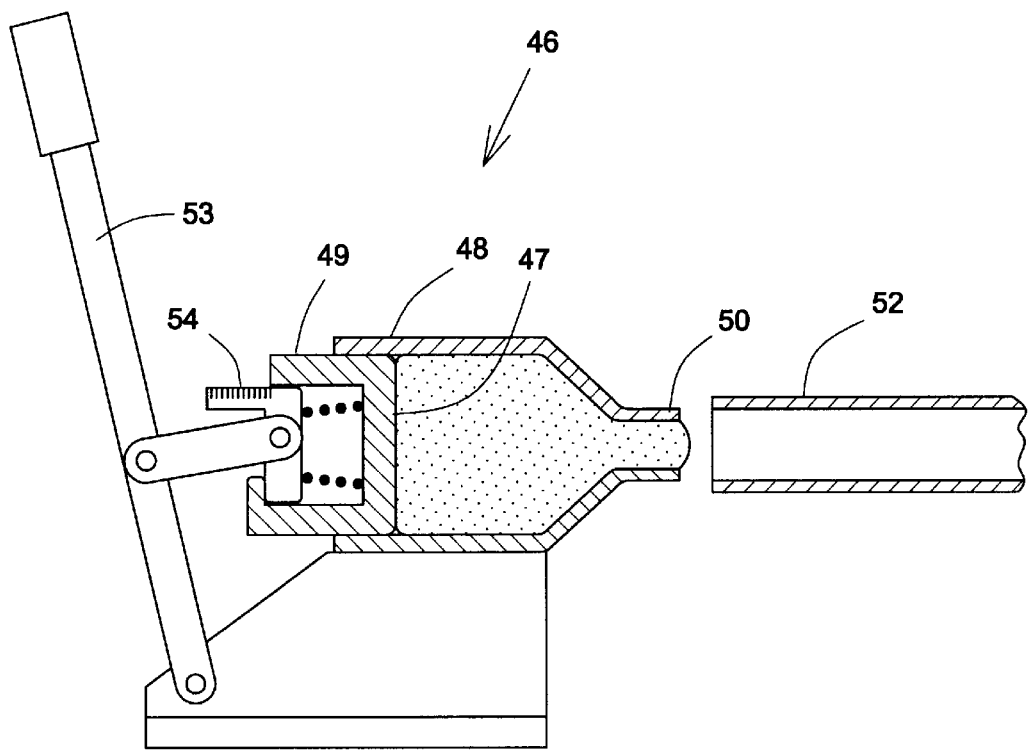
FIG. 10 is a diagrammatic sectional view of an inflation pump, for use during fitment of the hearing device of FIG. 1 into the ear.

Alternatively, the inflation pump 46 shown in FIG. 10 may be used. The inflation-fluid is a two-part silicone material. This is made as a two-part mixture from two component materials, which are brought together and mixed immediately prior to use. The mixture remains liquid enough to be pumped and injected for several minutes. In the use of the pump 46, the liquid mixture is sealed into a plastic bag 47, which is placed in the cylinder 48 of the pump. A plunger 49 engages the cylinder, and the bag is compressed thereby until a bubble of the plastic bag protrudes from the nozzle 50 of the pump. This is pierced or cut, and a nozzle tube 52 is placed over the nozzle. The other end of the nozzle tube is placed in the inflation tube 35 of the device in the client's ear. The (plastic) tubes fit together by being made size-on-size, which gives an adequate fit and seal in the context of the invention. The practitioner forces the liquid mixture from the bag into the cavity 26, by pressing the lever 53. The force or pressure can be read off the scale 54.

Preferably, to best ensure a perfect fit of the finished hearing device, a slight residual pressure should be left on the inflation-fluid as the fluid sets and cures (which takes several minutes). Preferably also, the hearing device should continue to be pressed inwards as the inflation-fluid sets and cures. (That is to say, the portion of the device 20 that fits outside the aperture of the ear canal should be pressed against the ear, i.e in effect pressed against the side of the head, while curing takes place.) These measures serve to leave the finished device of such shape and dimensions that, when the device is fully inserted into the ear, the device is very slightly drawn inwards into the ear.

The sheath as used in the embodiments described herein is elastic, and becomes stretched when the inflation-fluid is injected. Therefore, it might be the case that if the pressure is not maintained on the injection-fluid during curing and setting of the inflation-fluid, the stretch of the sheath might cause the sheath to become slightly slack in the ear-canal, at the critical time, i.e when the inflation-fluid is setting and solidifying.

Of course, the practitioner should see to it that the pressure of the injected fluid cannot damage the client. An inflation pressure of perhaps 5 psi is considered to give an excellent conformation of the sheath to the ear-canal, without incurring any danger of damage thereto.

When the inflation-fluid has set, the nozzle tube is withdrawn. Usually, the inflated hearing device is pulled out of the ear along with the nozzle tube. In that case, the practitioner pulls the nozzle tube 52 out of the inflation tube 35, thereby tearing or breaking the solidified inflation-fluid, and leaving a stump thereof within the inflation tube (as shown at 56 in FIG. 2). Sometimes, upon removing the nozzle tube, the stump might be torn off in the inflation tube while the device is left in the ear.

Figure 11:
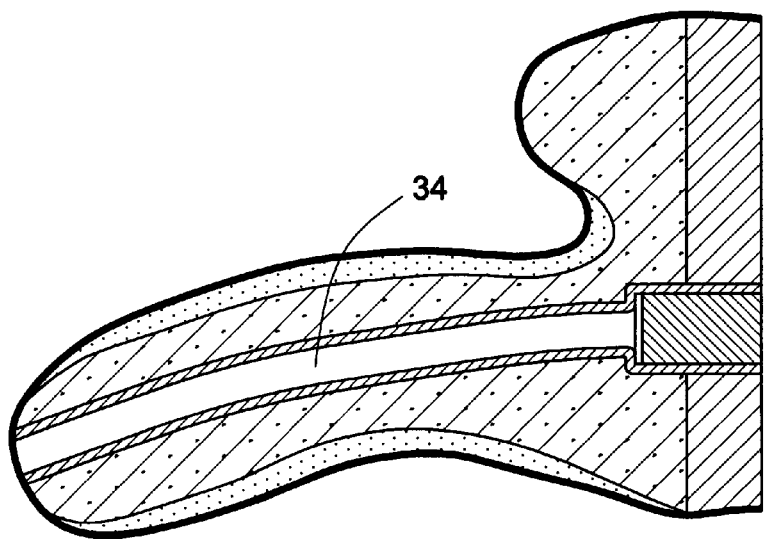
FIG. 11 is a cross-section showing another in-ear hearing device, which embodies the invention.

The hearing device shown in FIGS. 1–8 is acoustic-only, in the sense that no powered electronic components are present in the device. If the device is for use as a noise-protector, a solid plug can be inserted into the wider portion of the acoustic tube 34, thus blanking off the tube (FIG. 11). In that case, the intention is that all noise is attenuated by the protector. However, often what is wanted is that the dangerous hearing-damaging noise is attenuated, but that speech and perhaps other useful frequencies are less attenuated, or are enhanced. This can be done by shaping the acoustic tube 34 to give the appropriate resonances and filters. Of course, this is not easy, but a skilled expert at sound manipulation can, with some experiment, create a hearing protector that attenuates noise to comfortable levels, and still allows speech frequencies to pass, under many noise conditions as encountered in industry. In adapting the hearing device to a particular perosn, or to a particular noise situation, the expert may make use of commercially-available standard filters.

It should be noted that this kind of refinement of the hearing protector has hardly been possible hitherto, for the benefit of industrial workers. The fit of the conventional devices has been so poor that the device allowed so much sound energy to leak around the device, and through the ear-canal, that it was hardly worthwhile trying to create sophisticated acoustic filters. Either the fit of the device would allow sound energy to by-pass the device, with consequent damage to the hearing; or the fit of the device would be so tight that the wearer found it uncomfortable over a long period, and would take it out, with consequent damage to the hearing.

The fit of the hearing device as described herein, by contrast, on the other hand, can be expected to be virtually perfect. The device is actually formed, i.e finish-manufactured, while inside the very ear-canal in which it will be worn. This may be contrasted with the conventional custom-fitting process, in which an impression being taken of the ear-canal and then the device is manufactured at a remote location, from the impression, by subsequent moulding and furbishing processes.

Other benefits arise as a consequence of the fit between the hearing device and the ear-canal being virtually perfect. First, as mentioned, it is now worthwhile for the sound expert to devote effort to creating acoustic resonance chambers, etc, knowing that the chambers will not simply be by-passed by the noise waves. Also, it now becomes possible to measure the actual effect, at the ear-drum, of the hearing protection device. It was all very well for the manufacturers of conventional HPDs to claim that their products gave this or that degree of attenuation, under ideal conditions, but that was not what the user actually experienced.

The access-tube 32 shown in FIG. 2 not only can be used to allow air in the ear-canal to escape when the device is being fitted. The tube 32 can also serve to enable access for instruments, and particularly to enable a microphone probe to be inserted into the space 56 between the end of the device and the ear-drum. This microphone (not shown) can measure the actual effect of the hearing device; if the device is poorly fitted, that fact will be apparent in the spectrum of sounds as picked up by the microphone.

Thus, the practitioner has a non-subjective measure of the in-ear performance of the HPD. This can be very useful, not only from the standpoint that the results can be used in evidence in a case of a worker who claims compensation when his hearing has been damaged, but also from the standpoint of giving the practitioner objective feedback as to the effects of the measures he has taken, which is an effective tool for enabling him to improve those measures.

The instrument-access-tube 32 remains in place all the time, and is plugged when not in use to take readings, and when not needed for venting purposes.

The invention makes it economical for HPDs to be custom-fitted to every worker in a factory. The invention also permits the HPDs to be sophisticated. For example, sound engineers can make evaluations and recordings at every work station, and can tailor the device the worker will wear at that station to the particular noise conditions. If a worker attends several different stations, the best compromise for those different conditions can be determined; or alternatively, a worker may be provided with several different (pairs of) custom-fitted ear protectors, which he changes as he moves from station to station, the expectation being that at each station he will be well protected from noise.

For economic reasons, generally HPDs are passive. However, it can be contemplated that electronic components can be included in the device, which will assist in the sometimes-difficult task of masking and attenuating damaging noise while allowing speech (or other useful sounds) to pass.

Sometimes electrically powered components other than electronic amplifier components may be employed. In some work conditions, the noise is in the form of occasional loud bangs (in a press-shop, for instance) and a device for use in those conditions has an acoustic passageway that would be kept open most of the time. But as soon as a sensor picks up the onset or commencement of a loud bang, a relay closes the passageway for a moment. Thus, loud bangs are attenuated, but between-times the user enjoys full sound transmission. As has been found with some traditional types of noise filter, without the virtually-perfect fit provided by the invention, such measures could hardly be effective.

Figure 12:
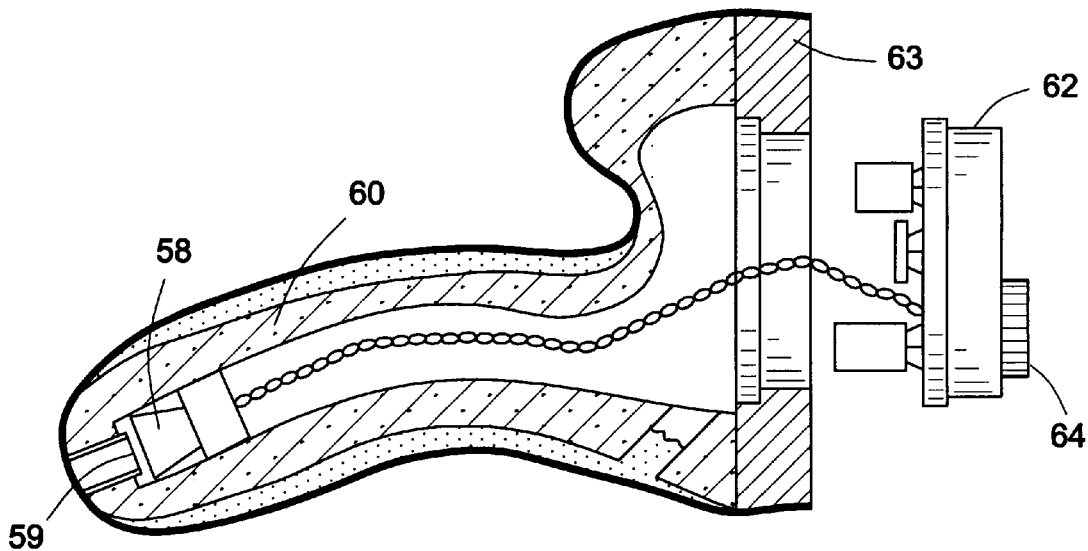
FIG. 12 is a cross-section showing a further in-ear hearing device, which also embodies the invention.

FIG. 12 shows a hearing-aid device in which a loudspeaker 58 is located at the end of the device, and the acoustic tube 59 is correspondingly short. The moulded core-form 60 in this case is moulded with a hollow interior. The electronic components, including the microphone of the hearing aid, the amplifier, and the battery, can be designed to fit in the hollow interior, or, as shown, can be located in a unit 62 which snaps into a recess in the end-plug 63. The hearing-aid user-controls 64 are accessible from outside.

The invention is applicable to other configurations of hearing aid. In one conventional hearing-aid configuration, the electronic components are all located outside the in-ear structure (usually in a behind-the-ear unit), and communicate with the in-ear structure by means of a plastic tube that slips into the open end of the acoustic tube 34. Alternatively, most of the electronic components can be in the behind-the-ear unit, and the connection from there is made by means of electrical wires to a loudspeaker that is physically located in the acoustic tube 34.

What is claimed is:
1. Hearing apparatus, which is suitable for fitment to the ear of a person, wherein:
   the apparatus includes an ear-unit, which includes a sheath, and includes an end-plug;
   the sheath is a moulded structure, and is moulded to a configuration which is suitable for insertion inside a person's ear-canal, the end-plug being so large as to be not suitable for insertion into the person's ear-canal;
   the sheath is hollow inside, and the sheath defines, with the end-plug, an internal enclosed hollow chamber;
   the structure of the sheath is such that the hollow chamber can be inflated, in that the sheath is able to expand radially, upon the chamber being pressurised;
   the sheath is so structured, as to its shape and size, that, with the hollow chamber not inflated, the sheath is able to pass loosely into the ear-canal of a person;
   the ear-unit includes an inflation-port, having a mouth which lies outside the end-plug, and which is accessible from outside the person's ear, when the sheath has been passed into the ear-canal of the person, and the inflation-port communicates with the hollow chamber;
   the apparatus includes an inflation-medium, which initially is a liquid, but which is able to set and cure to a solid;
   the apparatus includes an operable injector-means, which is so structured as to be suitable to be applied to the mouth of the inflation-port, and which is effective, when operated, then to inject the inflation-medium, as a liquid, under pressure, through the inflation-port, and into the hollow chamber, while the sheath lies disposed in the ear-canal of the person, thereby to inflate the sheath to an inflated condition, in the person's ear-canal, and for maintaining the inflation-medium in the chamber while the medium sets and cures;
   the inflation-medium has adhesive properties, and, after setting and curing to solid, in the person's ear-canal, the inflation-medium lies adhered to the inside surface of the hollow-chamber in the sheath;
   the injector-means is so structured as to be detachable, after the medium has set and cured, from the mouth of the inflation-port, and from the ear-unit;
   whereby, with the injector-means detached therefrom, the ear-unit, comprising the sheath, and the end-plug, and including the solid inflation-medium in the chamber, comprises a complete unitary structure, being a structure that is suitable for removal from, and for subsequent re-insertion into, the ear-canal of the person.
2. Hearing apparatus, which is suitable for fitment into the ear of a person, wherein:
   the apparatus includes an ear-unit, comprising a sheath and a core;
   the core comprises a main-portion, and an end-plug, located at a near end of the core;
   at a near end of the main-portion thereof, the main-portion is attached to the end-plug, and extends away from the end-plug;
   the sheath is generally tubular, and lies generally over and around the core;
   the apparatus includes a near-seal-means, for sealingly attaching a near-end-portion of the sheath to the near end of the core;
   the apparatus includes a far-seal-means, for sealingly attaching a far-end-portion of the sheath to the far end of the core;

between the near end and the far end, the sheath comprises a middle-portion, and the inside surface of the sheath is free of adherence to the outside surface of the core, over the middle portion;

the sheath is so positioned over and around the core as to define an annular chamber between the inside surface of the sheath and the outside surface of the core;

the annular chamber is closed at the near end by the near-seal-means, and is closed at the far end by the far-seal-means;

the disposition of the sheath on the core is such that the middle-portion of the sheath can be inflated, in that the middle-portion is able to expand radially away from the core, upon the annular-chamber being pressurised;

the ear-unit is so structured, as to its shape and size, that, with the annular chamber not inflated, the ear-unit is able to pass loosely into the ear-canal of a person;

the ear-unit includes an inflation-port, having a mouth which lies outside the end-plug, and which is accessible from outside the person's ear, when the ear-unit has been passed into the ear-canal of the person;

the apparatus includes an inflation-medium, which initially is a liquid, but which is able to set and cure to a solid;

the apparatus includes an operable injector-tool, which is so structured as to be suitable to be applied to the mouth of the inflation-port, and which is effective, when operated, then to inject the inflation-medium, as a liquid, under pressure, through the inflation-port, and into the annular chamber, while the ear-unit lies disposed in the ear-canal of the person, thereby to inflate the ear-unit to an inflated condition, in the person's ear canal, and as to be suitable for maintaining the inflation-medium in the chamber while the medium sets and cures;

the inflation-medium has adhesive properties, and, after setting and curing to solid, in the person's ear-canal, the inflation-medium lies adhered to the inside surface of the sheath and to the outside surface of the core;

the injector-tool is so structured as to be detachable, after the medium has set and cured, from the mouth of the inflation-port, and from the ear-unit;

whereby, with the injector-tool detached therefrom, the ear-unit, comprising the core and the sheath, and including the solid inflation-medium in the chamber therebetween, comprises a complete unitary structure, which is suitable for removal from, and for subsequent re-insertion into, the ear-canal of the person.

3. Apparatus of claim 2, wherein the ear-unit, upon detachment of the injector-tool therefrom, is complete in the sense that substantially no further manufacturing processing of the ear-unit is required for the ear-unit to be suitable for repeated insertion into, and removal from, the ear-canal of the person.

4. Apparatus of claim 2, wherein the inflation-port comprises an inflation-tube, which passes through the core, and the inflation-tube communicates the mouth of the inflation-port, in the end-plug, with the outside surface of the middle-portion of the core, and the inflation-tube opens into the annular chamber.

5. Apparatus of claim 4, wherein:

an in-tube portion of the now-cured medium is a portion that remains in the inflation-tube, and remains attached to the injector-tool, after the inflation-medium has cured;

the inflation-tube is so configured that, upon detachment of the injector-tool from the end plug, the in-tube portion of the now-cured medium breaks off, leaving a stump of the now-cured medium remaining in the inflation-tube.

6. Apparatus of claim 2, wherein.:

the sheath is in the form of a thin, flexible membrane, and the sheath, by itself, has substantially no inherent structural rigidity;

the core is of a form that is solid and rigid enough that the core has an inherent structural rigidity.

7. Apparatus of claim 6, wherein the sheath and the core are so dimensioned that, prior to inflation, the sheath lies stretched tightly over the core, to the extent that substantially no air lies trapped between the inside surface of the sheath and the outside surface of the core.

8. Apparatus of claim 6, wherein the core is elastomeric, and the core, though having some inherent structural rigidity, is also soft and squeezable.

9. Apparatus of claim 8, wherein the core is pre-moulded.

10. Apparatus of claim 2, wherein the core includes a sound-means, for transmitting sounds to the ear drum, and the sound-means includes a portion which is located at or near the far end of the in-ear-unit, and which faces the ear drum.

11. Apparatus of claim 10, wherein the sound-means includes a tube, running lengthwise through the core, and sealed from the annular chamber.

* * * * *